US012653489B2

(12) United States Patent
Cheng et al.

(10) Patent No.: US 12,653,489 B2
(45) Date of Patent: Jun. 16, 2026

(54) METHOD AND SYSTEM FOR ESTIMATING ENERGETIC HEMODYNAMIC PARAMETERS AND COMPUTER READABLE MEDIUM THEREOF

(71) Applicant: National Yang Ming Chiao Tung University, Hsinchu City (TW)

(72) Inventors: Hao-Min Cheng, Taipei City (TW); Jiun-Jr Wang, Taipei City (TW); Geng-Shi Jeng, New Taipei City (TW); Shao-Yuan Chuang, Changhua County (TW)

(73) Assignee: National Yang Ming Chiao Tung University, Hsinchu City (TW)

( * ) Notice: Subject to any disclaimer, the term of this patent is extended or adjusted under 35 U.S.C. 154(b) by 0 days.

(21) Appl. No.: 18/923,618

(22) Filed: Oct. 22, 2024

(65) Prior Publication Data

US 2026/0108227 A1 Apr. 23, 2026

(51) Int. Cl.
*A61B 8/06* (2006.01)
*A61B 8/00* (2006.01)
*A61B 8/08* (2006.01)

(52) U.S. Cl.
CPC .............. *A61B 8/06* (2013.01); *A61B 8/0891* (2013.01); *A61B 8/488* (2013.01)

(58) Field of Classification Search
CPC .................................. A61B 8/06; A61B 8/488
See application file for complete search history.

(56) References Cited

U.S. PATENT DOCUMENTS

| | | | |
|---|---|---|---|
| 6,176,832 B1 | 1/2001 | Habu | |
| 10,165,955 B2 | 1/2019 | Gladshtein | |
| 10,194,808 B1 * | 2/2019 | Thompson ......... A61B 5/02444 |
| 2023/0285001 A1 * | 9/2023 | Palanisamy ............ A61B 8/488 |
| 2023/0346330 A1 | 11/2023 | So | |

FOREIGN PATENT DOCUMENTS

| | | |
|---|---|---|
| CN | 111818854 | 10/2020 |
| CN | 108472012 | 9/2021 |
| CN | 115715170 | 2/2023 |
| TW | 1740600 | 9/2021 |

* cited by examiner

*Primary Examiner* — Rochelle D Turchen
(74) *Attorney, Agent, or Firm* — Winston Hsu

(57) ABSTRACT

The present disclosure provides a method for estimating energetic hemodynamic parameters, including: an ultrasound device obtaining a vascular diameter and a blood flow waveform from a subject; obtaining a blood flow velocity of the subject; a processor providing a volumetric flow rate, a pulse wave velocity (PWV), and a blood pressure waveform of the subject; and a processor obtaining the energetic hemodynamic parameters. The present disclosure further provides a system for estimating energetic hemodynamic parameters, including: an ultrasound device having an ultrasound probe and used to obtain a vascular diameter and a blood flow waveform from a subject; and a processor coupled to the ultrasound device and used to perform the method of the present disclosure. The present disclosure still further provides a computer readable medium storing a computer executable code, upon executed, the computer executable code implements the method of the present disclosure.

14 Claims, 8 Drawing Sheets

Aorta

Carotid artery

Aorta

Carotid artery

GFI=0.9983

-0.0715
(P=0.0014)

0.0281
(P=0.2046)

MoCA

Carotid pulsatility index

Carotid mean flow

-0.0371+
(P=0.0773)

$Z_{ao}$ 0.1526
(P<0.0001)

-0.0567
(P=0.0083)

GFI=0.9976

-0.0590
(P=0.0119)

0.0099
(P=0.6749)

MoCA

Carotid pulsatility index

Carotid mean flow 0.0559+
(P=0.0166)

$\Gamma_{Ao}$

-0.3475
(P<0.0001)

-0.3770
(P<0.0001)

GFI=0.9985

-0.1012
(P<0.0001)

0.0763
(P=0.0003)

MoCA

Carotid energy pulsatility index

Carotid mean energy

-0.0201+
(P=0.3591)

$Z_{ao}$ 0.2997
(P<0.0001)

0.0213
(P=0.2981)

GFI=0.9941

-0.099
(P<0.0001)

0.0586
(P=0.0120)

MoCA

Carotid energy pulsatility index

Carotid mean energy 0.0411+
(P=0.0733)

$\Gamma_{Ao}$

-0.1675
(P<0.0001)

0.3254
(P<0.0001)

+: direct effects

METHOD AND SYSTEM FOR ESTIMATING ENERGETIC HEMODYNAMIC PARAMETERS AND COMPUTER READABLE MEDIUM THEREOF

BACKGROUND OF THE INVENTION

1. Field of the Invention

The present disclosure relates to hemodynamic monitoring application, and more particularly to estimation of energetic hemodynamic parameters.

2. Description of the Prior Art

Hemodynamic analysis is critical in clinical application for assessment of the cardiovascular system and function of organ, and for medical management. Several studies have been conducted to evaluate hemodynamics from various perspectives, for example, conventional hemodynamic parameters, which may be calculated from blood pressure waveforms and blood flow waveforms. Conventionally, carotid artery blood pressure waveforms and blood flow waveforms are recorded in a non-invasive way by a tonometry device and a carotid artery ultrasound probe, respectively. The carotid artery blood pressure- and flow waveforms-based hemodynamic parameters are obtained via software package and manual interpretation analysis afterwards, which is difficult to conduct, time-consuming, and unable to be widely applied to clinical uses.

Thereafter, ultrasound technology is developed to estimate local pulse wave velocity (PWV) based on volumetric flow rate (Q) and arterial cross-sectional area (A), which has its limitations in determining vascular health and organ function. The association between pulsatile energy, generated from pulsatile pressure and pulsatile flow, and vascular health and organ function is still unknown; and there is currently lack of proper tools for estimating the pulsatile energy efficiently. Furthermore, although it is known that carotid artery blood pressure may be evaluated by conventional technology; carotid artery blood pressure can not be obtained from carotid artery ultrasound technology.

In view of the foregoing, there is an unmet need in the art to estimate energetic hemodynamic parameters efficiently for determining the association between energetic hemodynamic parameters and function of the body in clinical application.

SUMMARY OF THE INVENTION

To solve the aforementioned problems, the present disclosure provides a method for estimating energetic hemodynamic parameters, including: an ultrasound device obtaining a vascular diameter and a blood flow waveform from a subject; obtaining a blood flow velocity of the subject according to the blood flow waveform; a processor providing a volumetric flow rate, a pulse wave velocity (PWV), and a blood pressure waveform of the subject; and a processor obtaining the energetic hemodynamic parameters according to the vascular diameter, the blood flow waveform, the blood flow velocity, the volumetric flow rate, the pulse wave velocity (PWV), and the blood pressure waveform. The ultrasound device includes an ultrasound probe.

The present disclosure further provides a system for estimating energetic hemodynamic parameters, including: an ultrasound device and a processor. The ultrasound device includes an ultrasound probe and is used to obtain a vascular diameter and a blood flow waveform from a subject. The processor is coupled to the ultrasound device and is used to: obtain a blood flow velocity of the subject according to the blood flow waveform; provide a volumetric flow rate, a pulse wave velocity (PWV), and a blood pressure waveform of the subject; and obtain the energetic hemodynamic parameters according to the vascular diameter, the blood flow waveform, the blood flow velocity, the volumetric flow rate, the pulse wave velocity (PWV), and the blood pressure waveform.

The present disclosure further provides a computer readable medium storing a computer executable code, upon executed, the computer executable code implements a method including: obtaining a blood flow velocity of a subject according to a blood flow waveform of the subject; providing a volumetric flow rate, a pulse wave velocity (PWV), and a blood pressure waveform of the subject; and obtaining the energetic hemodynamic parameters according to a vascular diameter of the subject, the blood flow waveform, the blood flow velocity, the volumetric flow rate, the pulse wave velocity (PWV), and the blood pressure waveform. The vascular diameter and the blood flow waveform are obtained by an ultrasound device having an ultrasound probe.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
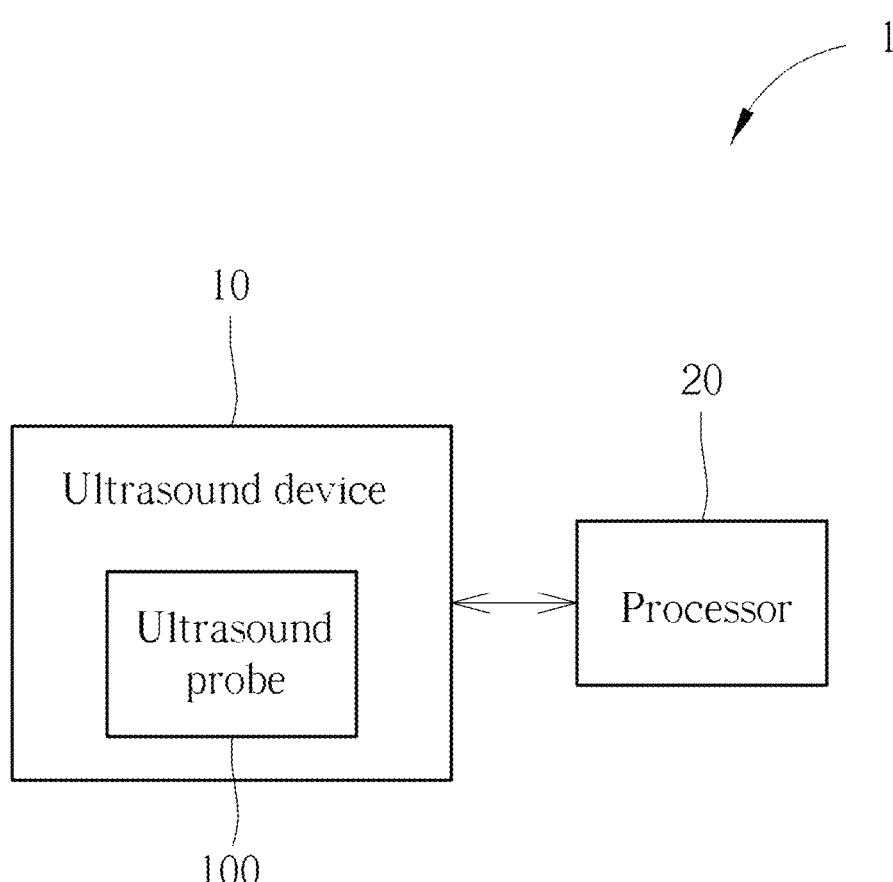
FIG. 1 is a schematic diagram illustrating an exemplifying structure of the system for estimation of energetic hemodynamic parameters in accordance with embodiments of the present disclosure.

The following embodiments are provided to illustrate the present disclosure in detail. A person having ordinary skill in the art can easily understand the advantages and effects of the present disclosure after reading the disclosure of this specification, and also can implement or apply in other different embodiments. Therefore, it is possible to modify and/or alter the following embodiments for carrying out this disclosure without contravening its scope for different aspects and applications, and any element or method within the scope of the present disclosure disclosed herein can combine with any other element or method disclosed in any embodiments of the present disclosure.

The proportional relationships, structures, sizes and other features shown in accompanying drawings of this disclosure are only used to illustrate embodiments describe herein, such that those with ordinary skill in the art can read and understand the present disclosure therefrom, of which are not intended to limit the scope of this disclosure. Any changes, modifications, or adjustments of said features, without affecting the designed purposes and effects of the present disclosure, should all fall within the scope of the technical content of this disclosure.

In order that the present invention may be more readily understood, certain terms are first defined. In addition, it should be noted that whenever a value or range of values of a parameter are recited, it is intended that values and ranges intermediate to the recited values are also intended to be part of this invention.

As used herein, the singular forms "a," "an," and "the" include plural referents, unless expressly and unequivocally limited to one referent. The term "or" is used interchangeably with the term "and/or" unless the context clearly indicates otherwise.

As used herein, the terms "comprise," "comprising," "include," "including," "have," "having," and any other variations thereof are intended to cover a non-exclusive inclusion. For example, when describing an object "comprises" a limitation, unless otherwise specified, it may additionally include other elements, components, structures, regions, units, modules, models, parts, devices, systems, steps, or connections, etc., and should not exclude other limitations.

As used herein, the phrase "at least one," in reference to a list of one or more elements, should be understood to mean at least one element selected from any one or more of the elements in the list of elements, but not necessarily including at least one of each element listed within the list of elements and not excluding any combinations of elements in the list of elements. This definition also allows that elements may optionally be present other than the elements identified within the list of elements to which the phrase "at least one" refers, whether related or unrelated to those elements identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

As used herein, the term "about" or "approximately" generally referring to the numerical value meant to encompass variations of 20%, ±10%, ±5%, ±1%, ±0.5%, or +0.1% from a given value or range. Such variations in the numerical value may occur by, e.g., the experimental error, the typical error in measuring or handling procedure for making compounds, compositions, concentrates, or formulations, the differences in the source, manufacture, or purity of starting materials or ingredients used in the present disclosure, or like considerations. Alternatively, the term "about" or "approximately" means within an acceptable standard error of the mean when considered by a person having ordinary skill in the art. Unless otherwise expressly specified, all of the numerical ranges, amounts, values and percentages such as those for quantities of materials, durations of time periods, temperatures, operating conditions, ratios of amounts, and the likes disclosed herein should be understood as modified in all instances by the term "about" or "approximately."

The numeral ranges used herein are inclusive and combinable, any numeral value that falls within the numeral scope herein could be taken as a maximum or minimum value to derive the sub-ranges therefrom. For example, the numeral range "20 s to 30 s" includes any sub-ranges between the minimum value of 20 s to the maximum value of 30 s, such as the sub-ranges from 20 s to 25 s, from 22 s to 28 s, from 25 s to 30 s and so on. In addition, a plurality of numeral values used herein can be optionally selected as maximum and minimum values to derive numerical ranges. For instance, the numerical ranges of 22 s to 25 s, 22 s to 28 s, and 25 s to 28 s can be derived from the numeral values of 22 s, 25 s, and 28 s.

As used herein, the terms "patient," "subject," "resident," and "individual" are used interchangeably. The term "subject" refers to a mammal. The mammal includes, but not limited to, humans, non-human primates, canines, felines, murines, bovines, equines, porcines, sheeps, deers, wolfs, foxes, and rabbits.

Unless otherwise specified, terms "carotid" and "carotid artery" used herein may be used interchangeably In at least one embodiment of the present disclosure, the ultrasound device may obtain the vascular diameter and the blood flow waveform by the ultrasound probe solely.

In at least one embodiment of the present disclosure, the method for estimating energetic hemodynamic parameters may further include the ultrasound probe placing at an artery of the subject.

In at least one embodiment of the present disclosure, the artery may be an elastic artery or a muscular artery.

In at least one embodiment of the present disclosure, the ultrasound device may implement ultrasound brightness mode (B-mode) imaging and/or ultrasound color Doppler mode imaging.

In at least one embodiment of the present disclosure, the ultrasound device may obtain the vascular diameter by the ultrasound brightness mode (B-mode) imaging.

In at least one embodiment of the present disclosure, the ultrasound device may obtain the blood flow waveform by the ultrasound color Doppler mode imaging.

In at least one embodiment of the present disclosure, the processor may obtain the volumetric flow rate according to formula I:

$$\pi \int_{-r_0}^{r_0} v(r) r \, dr, \quad \text{(formula I)}$$

wherein: $r_0$ is an initial vascular radius calculated from the vascular diameter; v(r) is a blood flow velocity polynomial; v is the blood flow velocity; r is a vascular radius; and dr is an infinitesimal change or an increment in the vascular radius.

In at least one embodiment of the present disclosure, the processor may obtain the pulse wave velocity (PWV) according to formula II: y=ax+b (formula II), wherein: y is the volumetric flow rate (Q); x is a vascular cross-sectional area (A); a is the pulse wave velocity (PWV); and b is a constant.

In at least one embodiment of the present disclosure, the processor may obtain the blood pressure waveform according to formula III:

$$P_n = P_0 + \frac{\rho c^2}{A_0} \sum_{i=1}^{n} \Delta A_i, \quad \text{(formula III)}$$

wherein: n is a n-th sampled point; $P_n$ is a blood pressure at the n-th sampled point; $P_0$ is an end diastolic pressure; $\rho$ is a blood density; c is the pulse wave velocity (PWV); A is a vascular cross-sectional area (A); $A_0$ is an initial vascular cross-sectional area; and $\Delta A_i = A_i - A_{i-1}$.

In at least one embodiment of the present disclosure, the ultrasound device may be configured to obtain the vascular diameter and the blood flow waveform by the ultrasound probe solely.

In at least one embodiment of the present disclosure, the vascular diameter and the blood flow waveform may be obtained from an artery of the subject.

In at least one embodiment of the present disclosure, the ultrasound device may be configured to implement ultrasound brightness mode (B-mode) imaging and/or ultrasound color Doppler mode imaging.

In at least one embodiment of the present disclosure, the ultrasound device may be configured to obtain the vascular diameter by the ultrasound brightness mode (B-mode) imaging.

In at least one embodiment of the present disclosure, the ultrasound device may be configured to obtain the blood flow waveform by the ultrasound color Doppler mode imaging.

In at least one embodiment of the present disclosure, the processor may be configured to obtain the volumetric flow rate according to formula I:

$$\pi \int_{-r_0}^{r_0} v(r) r \, dr, \quad \text{(formula I)}$$

wherein: $r_0$ is an initial vascular radius calculated from the vascular diameter; v(r) is a blood flow velocity polynomial; v is the blood flow velocity; r is a vascular radius; and dr is an infinitesimal change or an increment in the vascular radius.

In at least one embodiment of the present disclosure, the processor may be configured to obtain the pulse wave velocity (PWV) according to formula II: y=ax+b (formula II), wherein: y is a volumetric flow rate (Q); x is a vascular cross-sectional area (A); a is the pulse wave velocity (PWV); and b is a constant.

In at least one embodiment of the present disclosure, the processor may be configured to the blood pressure waveform according to formula III:

$$P_n = P_0 + \frac{\rho c^2}{A_0} \sum_{i=1}^{n} \Delta A_i, \quad \text{(formula III)}$$

wherein: n is a n-th sampled point; $P_n$ is a blood pressure at the n-th sampled point; $P_0$ is an end diastolic pressure; $\rho$ is a blood density; c is the pulse wave velocity (PWV); A is a vascular cross-sectional area (A); $A_0$ is an initial vascular cross-sectional area; and $\Delta A_i = A_i - A_{i-1}$.

Referring to FIG. 1, a system for estimating energetic hemodynamic parameters 1 is illustrated, including an ultrasound device 10 having an ultrasound probe 100 and a processor 20. Described elements of the system for estimation of energetic hemodynamic parameters 1 may be connected to each other via any suitable wired or wireless means, of which the present disclosure is not limited thereto.

In some embodiments, the elements of the system may be individually realized as any suitable computing device, apparatus, program, system, or the like, but the present disclosure is not limited thereto. For example, the ultrasound device and the processor may be integrated instead of being realized as two distinct units. Nevertheless, without straying from the operation philosophy of the present disclosure, the configuration of said elements of the system may be realized in any suitable forms and should not be restrictive to the scope of the present disclosure.

In some embodiments, technique of estimating the energetic hemodynamic parameters is paired with a carotid ultrasound probe. Continuous carotid artery blood pressure waveform and carotid artery blood flow waveform during systolic and diastolic phases are obtained in 4 to 5 cardiac cycles by placing the carotid ultrasound probe in the corresponding part of the common carotid artery in a longitudinal view. Accordingly, the energetic hemodynamic parameters can be calculated simultaneously via combination of the carotid artery blood pressure waveform and carotid artery blood flow waveform.

In some embodiments, carotid artery blood pressure waveform-based variables, such as central systolic pressure, pulse pressure, and wave reflected indices, may be calculated from the carotid artery blood pressure waveform.

In some embodiments, carotid artery blood flow waveform-based variables, such as peak systolic velocity, end diastolic velocity, mean velocity, mean flow, pulsatility index and resistance index, may be calculated from the carotid artery blood flow waveform.

7

Figure 2:
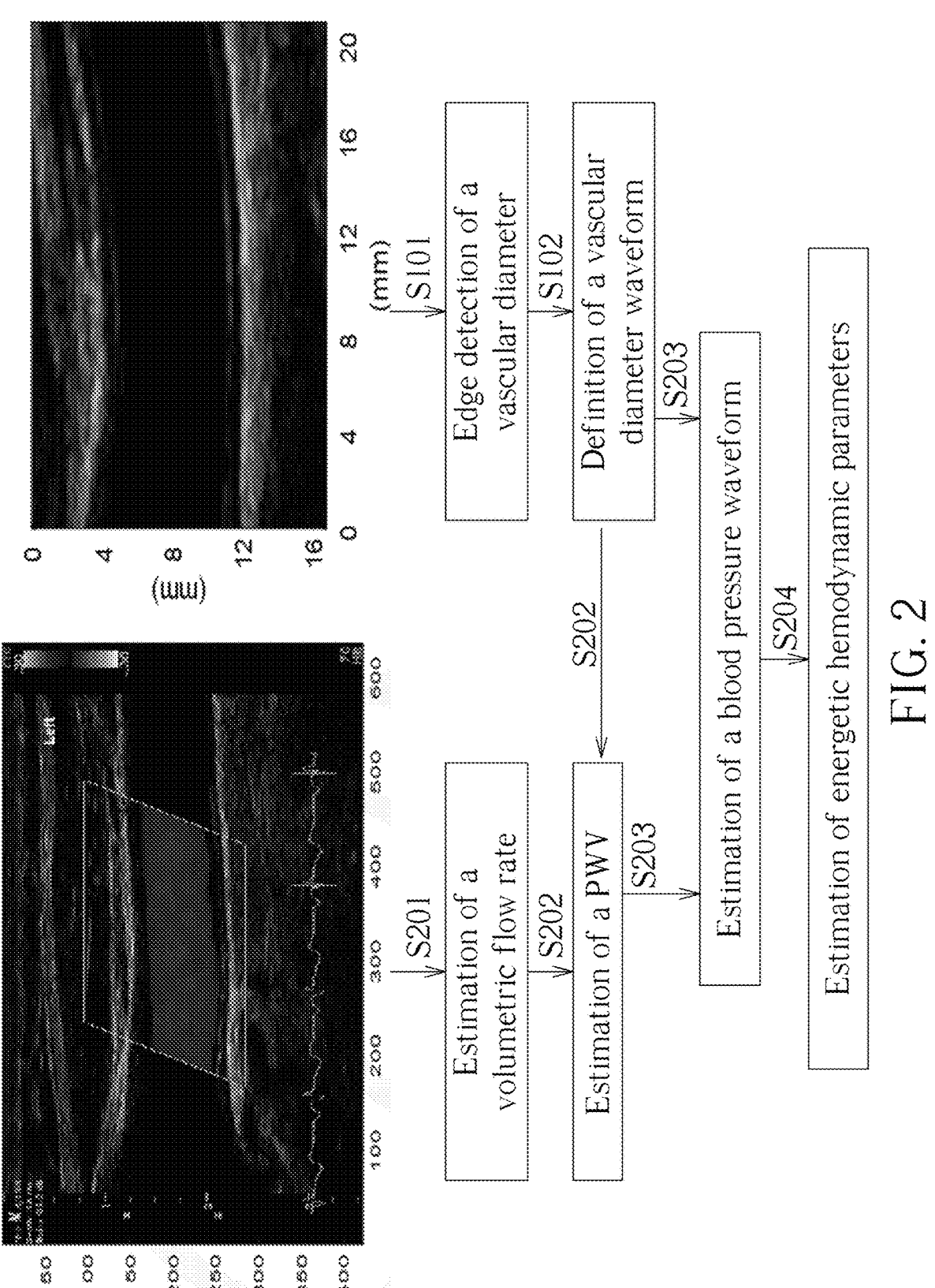
FIG. 2 is a flow chart describing steps for estimation of energetic hemodynamic parameters in accordance with embodiments of the present disclosure.

Referring to FIG. 2, a flow chart describing steps for estimation of energetic hemodynamic parameters utilizing elements of the system 1 is disclosed, and the following paragraphs illustrate execution details for each step by reference.

In some embodiments, the vascular diameter (e.g., carotid arterial diameter) is measured by edge detection and speckle-tracking imaging on ultrasound brightness mode (B-mode) imaging.

Step 101 (S101) denotes that vascular wall is detected by edge detection on ultrasound brightness mode (B-mode) imaging.

Step 102 (S102) denotes that various tracking points of the corresponding upper and lower vascular wall are selected based on the results of the edge detection; the temporal trajectory of each group of the tracking points is estimated by the speckle-tracking imaging, thereby obtaining a movement trajectory of the tracking points; a difference of the tracking points of the corresponding upper and lower vascular wall is estimated afterwards for defining a vascular diameter waveform.

In some embodiments, the blood flow velocity is measured by ultrasound color Doppler mode imaging; the volumetric flow rate is calculated via formula I of the present disclosure based on the blood flow velocity; and the pulse wave velocity (PWV) is calculated via formula II of the present disclosure based on the volumetric flow rate.

Step 201 (S201) denotes that the blood flow velocity at every time point is measured by ultrasound color Doppler mode imaging and the volumetric flow rate is calculated via formula I:

$$\pi \int_{-r_0}^{r_0} v(r) r \, dr, \qquad (I)$$

and $r_0$ is an initial vascular radius calculated from the vascular diameter; $v(r)$ is a blood flow velocity polynomial; $v$ is the blood flow velocity; $r$ is a vascular radius; and dr is an infinitesimal change or an increment in the vascular radius.

Step 202 (S202) denotes that the pulse wave velocity (PWV) is calculated via formula II: $y=ax+b$ (II), and y is the volumetric flow rate (Q); x is a vascular cross-sectional area (A); a is the pulse wave velocity (PWV); and b is a constant.

Step 203 (S203) denotes that the blood pressure waveform is provided based on the pulse wave velocity (PWV) and the vascular diameter waveform, and calculated via formula III:

$$P_n = P_0 + \frac{\rho c^2}{A_0} \sum_{i=1}^{n} \Delta A_i, \qquad (III)$$

and n is a n-th sampled point; $P_n$ is a blood pressure at the n-th sampled point; $P_0$ is an end diastolic pressure; $\rho$ is a blood density; c is the pulse wave velocity (PWV); A is a vascular cross-sectional area (A); $A_0$ is an initial vascular cross-sectional area; and $\Delta A_i = A_i - A_{i-1}$.

Step 204 (S204) denotes that the energetic hemodynamic parameters are provided based on the vascular diameter, the blood flow waveform, the blood flow velocity, the volumetric flow rate, the pulse wave velocity (PWV), and the blood pressure waveform.

In some embodiments, the energetic hemodynamic parameters may include hydraulic mean, pulsatile energy, total energy, pulsatility index (PI), characteristic impedance, and/or vascular resistance, but the present disclosure is not limited thereto.

In some embodiments, the energetic hemodynamic parameters, e.g., pulsatile energy, may be obtained according to the blood flow waveform and blood pressure waveform with commercial ultrasound probe efficiently and applied in clinical care, in order to reduce the difficulty and time of analysis.

In some embodiments, the pulsatile energy may have an impact on the organs of the body.

In some embodiments, using carotid artery ultrasound probe for continuously monitoring and analyzing hemodynamics to obtain parameters such as blood pressure waveform, blood flow waveform, and energetic hemodynamic parameters may achieve a non-invasive monitoring method. Combining results of hemodynamic analysis, e.g., the energetic hemodynamic parameters, with treatment regimen may improve the prediction of the likely course of a medical condition of a patient, thereby making an accurate prognosis; and may perform medical decisions more effectively.

In some embodiments, the method and system of the present disclosure may be incorporated with a wearable device, e.g., smartwatch or wearable ultrasound device, thereby collecting and analyzing the aforementioned parameters obtained from a subject. Accordingly, the medical personnel may determine the medical condition of the subject efficiently.

In at least one embodiment of the present disclosure, the energetic hemodynamic parameters may be correlated with vascular health and cognitive function, and an exemplifying embodiment demonstrating the correlation between the energetic hemodynamic parameters provided by the present disclosure and cognitive function is illustrated below.

In some embodiments, blood pressure measurement or blood flow measurement has been associated with vascular health and cognitive function. Energetic hemodynamic parameters may provide a more nuanced understanding and stronger correlation with cognitive function, in comparisons with conventional aortic and carotid pressure and flow parameters. The cognitive function of 1858 subjects is assessed via MoCA method, and central aortic and carotid pressure and flow waveforms thereof are measured. In addition to various blood pressure waveform- and blood flow waveform-based parameters, energetic hemodynamic parameters are calculated through integration of pressure multiplying flow with respect to time. The energetic hemodynamic parameters, particularly aortic and carotid mean and pulsatile energy, and pulsatility index (PI), are significantly associated with MoCA score more than any aortic and carotid pressure waveform- and flow waveform-based parameters, after adjusting for age, sex, education, depression score, heart rate, BMI, high density lipoprotein- (HDL-) cholesterol, and glucose levels. MoCA exhibited a strong positive relationship with carotid mean energy (standardized beta=0.053, P=0.0253) and a negative relationship with carotid energy PI (standardized beta=−0.093, P=0.0002), exceeding the association with all traditional pressure waveform- or flow-based parameters. Aortic pressure reflection coefficient at the aorto-carotid junction is positively correlated with carotid mean energy and negatively correlated with PI. Aortic characteristic impedance positively correlated with carotid energy PI but not mean energy. The present disclosure indicates that the energetic hemodynamic parameters, particularly carotid mean energy and carotid energy PI, have a stronger association with MoCA scores than traditional pressure- or flow-based metrics, i.e., pressure and flow parameters. The correlation between the energetic hemodynamic parameters with cognitive function is notably influenced by the properties of the aorto-carotid interface.

In some embodiments, cognitive decline and dementia are escalating global health concerns, especially within aging populations. A robust body of evidence links vascular dementia with hemodynamic abnormalities stemming from various cardiovascular conditions. High blood pressure, for example, compromises the cerebral vasculature and predisposes individuals to cognitive impairment, especially when it develops earlier in life.

In some embodiments, given the role of carotid hemodynamics in cerebral blood supply, the carotid hemodynamics has been a focus of study traditionally. Changes in carotid pressure and flow waveforms have been linked to cognitive impairment. As a result, different parameters derived from pressure or flow waveform have been developed to improve the ability to predict patient outcomes. It is demonstrated that lower carotid flow velocity is frequently associated with smaller cerebral white matter and gray matter volume, and has been regarded as a strong indicator of brain atrophy and an effective predictor of increased risk of stroke. It has emphasized the associations of parameters, such as pressure and flow pulsatility indexes (PIs), with cerebrovascular diseases and cognitive decline.

In some embodiments, the "impedance mismatch" hypothesis illustrates vascular aging-related target organ damage. The hypothesis states that pulsatile energy is not fully transmitted into the distal vasculature because impedance mismatch at the junction of the highly compliant aorta and relatively stiff first-generation branch vessels limits transmission of pulsatile power/energy into the carotid artery. Vascular aging of proximal aorta erodes impedance mismatch and promotes transmission of excess pulsatile energy into the carotid arteries. An inclusive comprehension of systemic or organ hemodynamics typically necessitates the acquisition of both blood pressure and flow data. Traditional metrics, which are primarily derived from pressure or flow alone, might not totally include the complex interaction between vascular and cognitive functions. Therefore, the present disclosure demonstrates that the energetic hemodynamic parameters may provide a more comprehensive and nuanced framework for analyzing the complex relationship and patient's outcome prediction.

Materials and Methods

Study Cohorts

The study cohort of the present disclosure includes two study populations, the Cardiovascular and Disease Risk Factors Two-Township Study (CVDFACTS) and the Longitudinal Aging Study of Taipei (LAST). CVDFACTS is an ongoing longitudinal study of the risk factors and pathogenesis of cardiovascular disease in two Taiwanese cities, Chu-Dung (a Hakka community) and Pu-Tzu (a Fukienese community). Residents who are aged 30 and over, and previously participated in one or more of CVDFACTS surveys are recruited from 2017 through 2020. The Longitudinal Aging Study of Taipei (LAST) is an ongoing community-based study that is initiated by Aging and Health Research Center of the National Yang Ming Chiao Tung University from May 2016 to December 2019, a total of 1532 community volunteers are invited to participate the first wave of the study. The criteria for including and excluding participants in two cohorts are as follows: the inclusion criteria are individuals who agreed to take part in the cohort studies and follow-up. The exclusion criteria consist of individuals with poor activities of daily living, long-term bedridden individuals, those unable to complete the questionnaire due to communication challenges, individuals with a life expectancy of less than 6 months, arrhythmia, heart failure, severe valvular heart disease, individuals diagnosed with dementia, and other neurodegenerative diseases, such as Parkinson's disease.

For the cardiovascular hemodynamic assessments, these two study cohorts have adopted the same study protocol, which has been approved by the Institutional Review Board of National Yang Ming Chiao Tung University. Each participant is well-informed, and a written consent is obtained before the study.

All subjects are scheduled for two visits within 3 months for the study. Information of personal characteristics, prior medical history, anthropometric measurements, cognitive function, and fasting blood tests are collected during the first visit. Medical history, particularly stroke and heart diseases, is acquired by structured questionnaires. An example is as follows: "Do you have heart disease diagnosed by a physician at a clinic or hospital?" Cardiovascular hemodynamic measurements are conducted during the second visit. The structured questionnaires are used, the Center for Epidemiologic Studies Depression Scale and Taiwanese Depression Scale in LAST cohort and CVDFACTS cohort, respectively, to measure depression. The depression scales of these two cohorts are then normalized for further analysis.

Cognitive Function

The global cognitive function is evaluated using the Montreal Cognitive Assessment (MoCA) protocol with the Chinese version specifically used in Taiwan (Tsai J C, Chen C W, Chu H, Yang H L, Chung M H, Liao Y M, et al. Comparing the sensitivity, specificity, and predictive values of the montreal cognitive assessment and mini-mental state examination when screening people for mild cognitive impairment and dementia in Chinese population. Arch Psychiatr Nurs. 2016; 30:486-91), through face-to-face interview by dedicated and qualified nurses adherent to the standardized study guide. The MoCA is constituted by 20 items clustered into 7 subgroups, each dedicated to one aspect of cognitive function, namely executive function/visuospatial ability (5 points), attention (6 points), animal naming (3 points), language (3 points), abstraction (2 points), short-term memory (5 points), and orientation (6 points) with a total score of 30 points (Folstein M F, Folstein S E, McHugh P R. "Mini-mental state". A practical method for grading the cognitive state of patients for the clinician. J Psychiatr Res. 1975; 12:189-98).

Echocardiography

All participants receive transthoracic echocardiography performed by an experienced sonographer. All images are acquired using a commercially available machine (HD11 XE Ultrasound system, Koninklijke Philips N.V) and digitized using the TomTec Image-Arena™ Software 4.0 (TomTec Imaging Systems GmbH, Munich, Germany) by the same sonographer. Left ventricular (LV) volume is acquired by tracing the endocardial border of the left ventricle at both the end-diastole and end-systole, then summing up a stack of elliptical disks in apical 4-chamber view. The determination of LV ejection fraction involves calculating the discrepancy between the volume of the left ventricle at the end of diastole and the volume at the end of systole. Doppler-derived stroke volume is the product of the cross-sectional area and the velocity, calculated via Doppler signal acquired at the LV outflow tract during systole. Doppler-derived cardiac output is calculated as the product of stroke volume and heart rate. Cardiac index (CI) is calculated as cardiac output divided by the body surface area.

Arterial Stiffness

Arterial waveforms at the right common carotid artery (CCA) and the right femoral artery are recorded in sequence, by means of applanation tonometry using a pencil-type tonometer, a high-fidelity strain-gauge transducer at the flat tip of 7-mm-diameter (SPC-350, Millar Instruments Inc, Texas). Body surface measurements from carotid to femoral pulse recording sites are obtained by tape measure. Carotid-femoral pulse wave velocity (cf-PWV) is calculated as the distance between the two measurement sites, divided by the foot-to-foot wave transit time. Transit time is calibrated by the simultaneously recorded ECG, and aligned via a custom-designed software on a commercial software package (Matlab, version 4.2, The MathWorks, Inc.). Data Acquisition and Analysis Each recording lasted for about 20 s to 30 s (5 to 6 respiratory cycles) to ensure steady and high-quality pulse waveforms. Each waveform admitted for subsequent hemodynamic analysis is an average of 10 consecutive steady waveforms. The aortic pressure is determined by the tonometry waveform measured at the right CCA, calibrated by simultaneously measured mean and diastolic pressure of the brachial cuff pressure. Measurements of central aortic and carotid blood flows are performed by the same healthcare professional to maintain quality consistency. Central aortic blood flow, is determined as the Doppler flow velocity, measured using a pulsed-wave Doppler echocardiography at the LV outflow tract in an apical five-chamber view, multiplied by the cross-sectional area at the LV outflow tract on a parasternal long-axis views. The flow velocity (waveform-derived) is measured from the envelope as a spatially averaged mean value for the subsequent calculation of the flow PI and energetic hemodynamic parameters. The left and right common carotid flows are determined by the Doppler velocity waveform, recorded using a linear array probe with 3.1-10.0 MHz imaging frequency in the longitudinal view. The sample volume is placed at the center of the CCA around 1 cm proximal to the carotid bulb. Flow velocities are multiplied by the respective carotid lumen cross-sectional area to get volumetric flow rate. The carotid arterial diameter is measured from the intima-lumen interface of the near wall to the lumen-intima interface of the far wall. All Doppler measurements are obtained with an insonation angle maintained ≤60°. The carotid flow waveform images are digitized and transformed into a signal-averaged flow spectrum in the MATLAB program. Each velocity waveform admitted for subsequent analysis is an average of 10 consecutive waveforms. Since the pressure at ascending aorta is largely comparable to the pressure at carotid artery, the measured carotid arterial pressure waveform is adopted as the aortic pressure waveform to be paired with the corresponding aortic flow for hemodynamic analysis. Given that the passage of a wave causes simultaneous changes in both pressure and flow waveform, arterial pressure waveform is shifted in time so that the onset of systolic pressure matches that of the blood flow waveform. For carotid hemodynamic analysis, the carotid blood flow admitted for hemodynamic analysis is the sum of both the left and right carotid blood flows.

Hemodynamic Analysis

The Mean and Pulsatile Hydraulic Energy

The hydraulic mean, pulsatile energy, and total energy for one cardiac cycle are calculated, and the calculation is consistent with those power-based parameters adopted by Haidar et al. (Haidar M A, van Buchem M A, Sigurdsson S, Gotal J D, Gudnason V, Launer U, et al. Wave reflection at the origin of a first generation branch artery and target organ protection: the AGES Reykjavik Study. Hypertension. 2021; 77:1169-77). To calculate the hydraulic mean and pulsatile energy for one cardiac cycle, the measured pressure P (t) and blood flow Q (t) waveforms are first separated into respective mean and pulsatile components:

$$P(t) = \overline{P} + P_p(t)$$

$$Q(t) = \overline{Q} + Q_p(t)$$

Total and pulsatile hydraulic energy, E, of one cardiac cycle, T, is calculated as the product of pressure P (t) and flow Q (t) or pulsatile pressure $P_p$ (t) and flow $Q_p$ (t), respectively, integrated with respect to time t over T. Calculations are repeated for both aorta and carotid artery. In addition, an effective accumulating "mean" energy, as P Q t is computed (FIG. 3A to FIG. 3D). FIG. 3A to FIG. 3D provides a detailed depiction of the pressure, flow, and energy waveforms at the aorta and carotid arteries. The relevant equations are provided below:

$$\text{Power } (t) = P(t) \times Q(t)$$

$$E = \int_{t=0}^{T} P(t) \times Q(t) dt$$

$$\overline{E} = \int_{t=0}^{T} \overline{P}(t) \times \overline{Q}(t) dt$$

$$E_p = \int_{t=0}^{T} P_p(t) \times Q_p(t) dt$$

$$E_{potential}(t) = E(t) - \overline{E}(t) - E_p(t)$$

$$E\_PI = \frac{E_p}{\overline{E}}$$

Figure 3A:
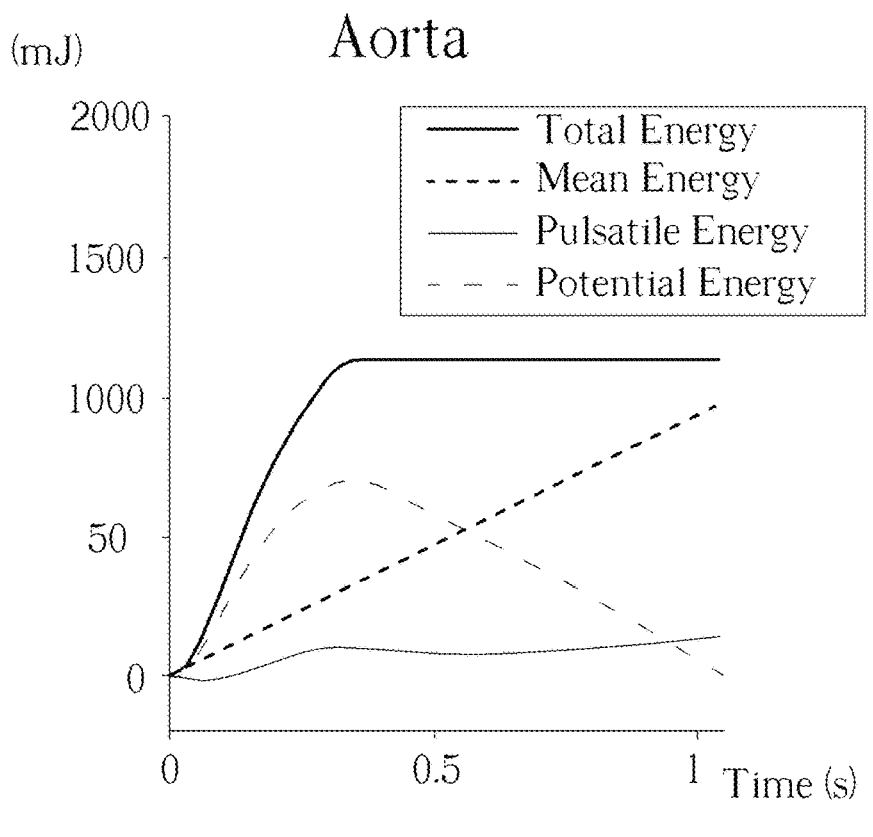
FIG. 3A to FIG. 3D are graphs presenting energetic hemodynamic parameters calculated at the central aorta and carotid artery as a function of time in accordance with embodiments of the present disclosure.
Figure 3A:
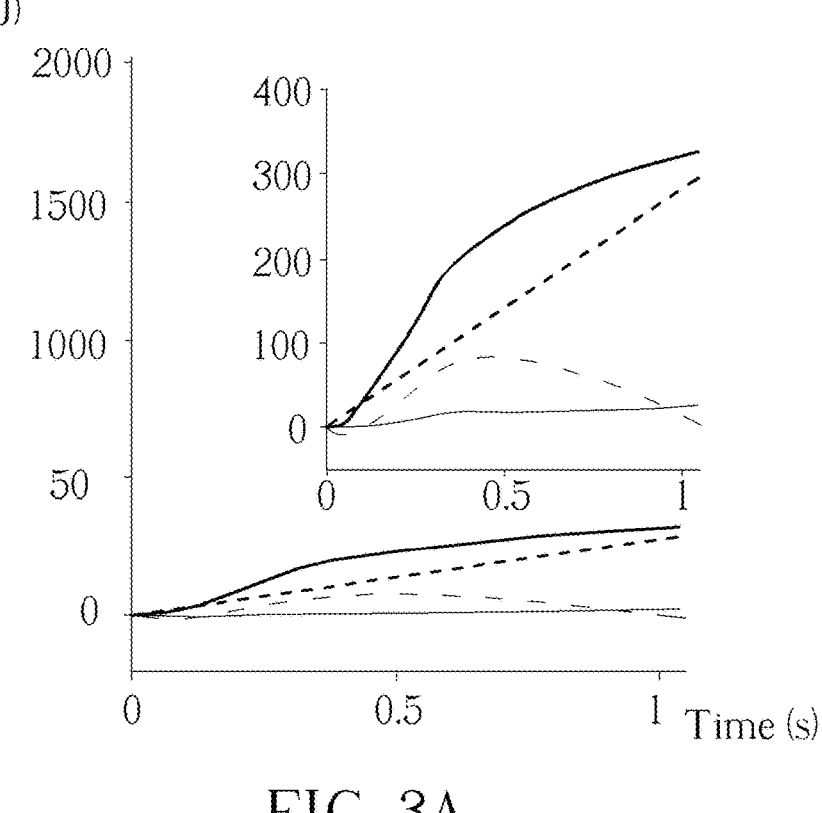
Figure 3B:
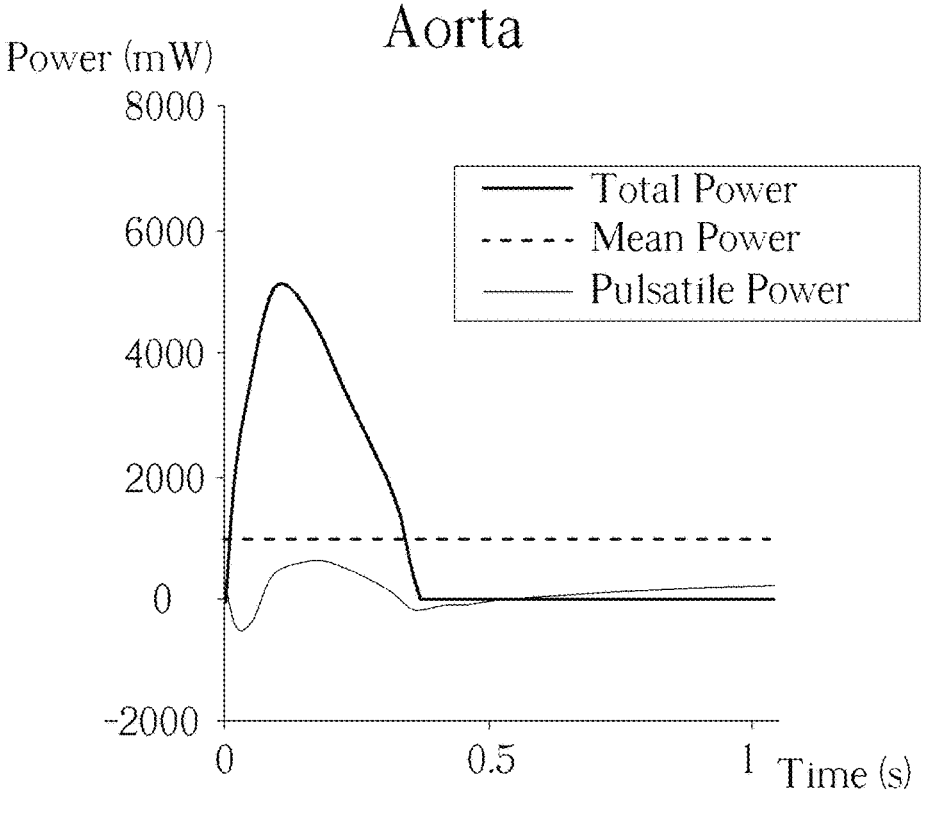
Figure 3C:
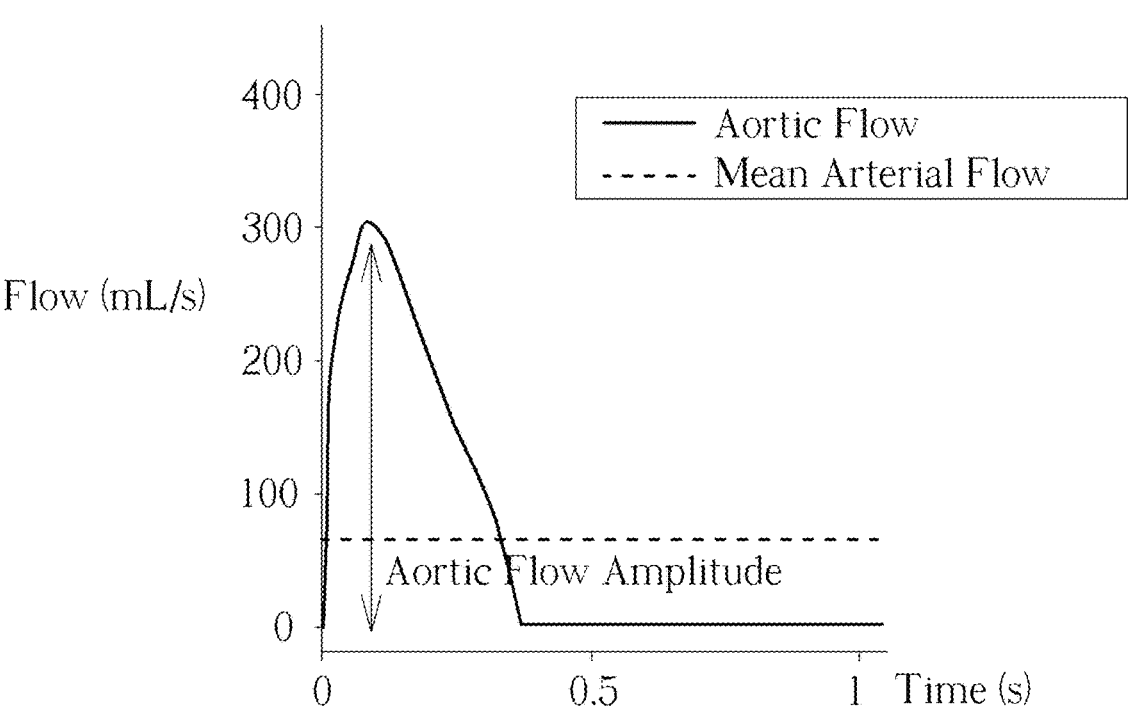
Figure 3C:
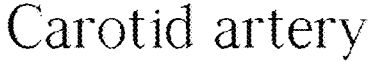
Figure 3C:
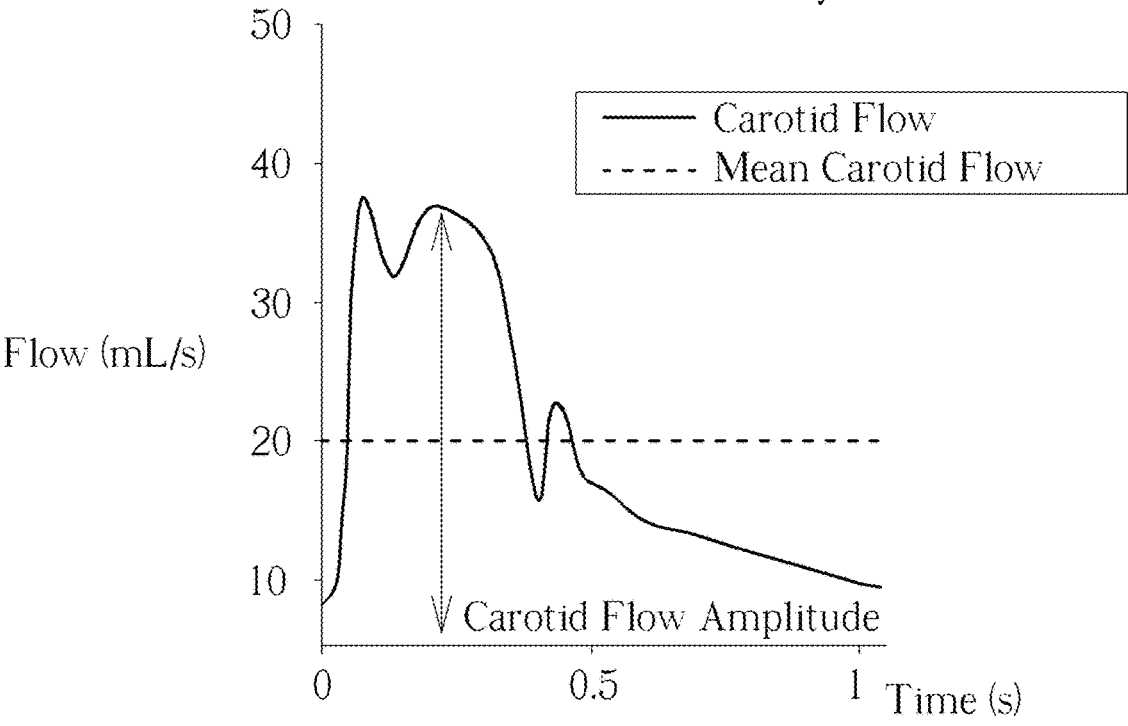
Figure 3D:
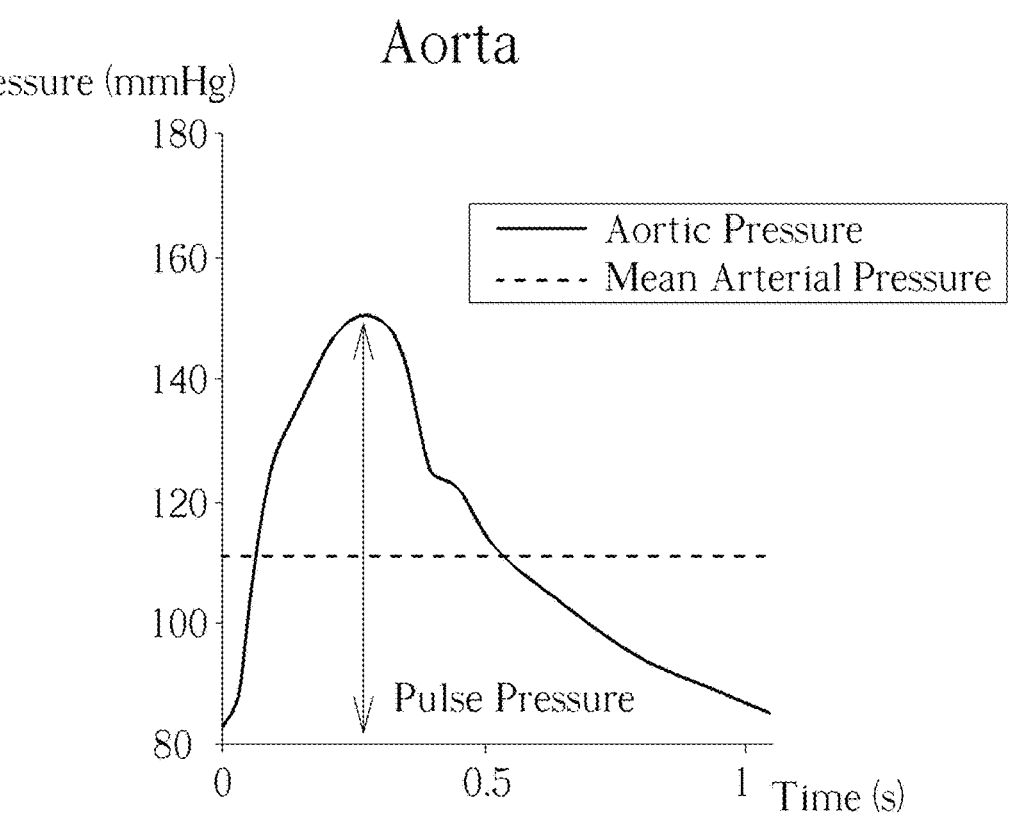

Referring to FIG. 3A to FIG. 3D, the first step is to calculate the total, mean, and pulsatile power as a function of time (FIG. 3B). The total power (thick solid curve) is calculated as the product of concurrent aortic pressure (thick solid curve; FIG. 3D) and aortic flow (thick solid curve; FIG. 3C). Similarly, the mean power (densely dashed curve) and pulsatile power (solid curve) are calculated as the product of concurrent mean pressure and mean flow (densely dashed curve) and concurrent pulsatile pressure and pulsatile flow, respectively. The second step is to calculate the total, mean, and pulsatile energy, by integrating the total, mean, and pulsatile power with respect to time (FIG. 3A). The third step, the potential energy as a function of time (loosely dashed curve) is calculated as the instantaneous difference between the total energy (thick solid curve) and the sum of the mean (densely dashed curve) and pulsatile energy (solid curve; FIG. 3A). Note that the total energy is not equal to mean energy plus pulsatile energy until the end of a cycle. Aortic and Carotid Wave Pressure, Flow and Energy Reflection, and Reflection Coefficients Aorto-carotid junction is simplified by a bifurcation, by which the central aorta is presumed branching into two asymmetric daughter vessels, a larger downstream thoracic aorta, and a smaller carotid artery. The carotid blood flow is calculated as a linear sum of both the left and right carotid flow since both sides of blood flow influenced cognitive function.

The aortic forward-going wave (defined as the direction of the mean blood flow) pressure reflection coefficient at the aorto-carotid junction, $\Gamma_{Ao}$, is calculated as $$\Gamma_{Ao} = \frac{A_{Ao} - A_{carotid} - A_{thoracic}}{A_{Ao} + A_{carotid} + A_{thoracic}}$$

where $A_{Ao}$, $A_{carotid}$, $A_{thoracic}$ are the admittance of the proximal aorta, the carotid artery and the downstream thoracic aorta, respectively. The admittance is the reciprocal of impedance. At aorta and carotid artery, admittance is calculated as the averaged ratio of magnitudes of flow to magnitudes of pressure from the 2nd harmonic through the 10th harmonic in frequency domain. At thoracic aorta, admittance is calculated as $A_{Ao}$ multiplied by the ratio of thoracic mean flow, which is the difference between the aortic mean flow and the carotid mean flow, divided by aortic mean flow, following the assumption that the local pulse wave velocity and mean flow velocity are presumed uniform across aorta just proximal of the bifurcation junction and distal thoracic artery. By definition, the aggregate forward-going flow wave reflection coefficient at the aorto-carotid junction is $\Gamma_{Ao}$.

Statistical Methods

Continuous and categorical characteristics of the sample are described by mean (standard deviation) and percentage, respectively. For the baseline model, the partial correlation coefficients between MoCA score and aorta-carotid arterial hemodynamics are computed by adjusting for age, sex, education, depression score, and heart rate. For the fully adjusted model, other potential confounders including body mass index, and low density lipoprotein- (LDL-) cholesterol, and fasting glucose are further adjusted for the associations between MoCA score and aorta-carotid arterial hemodynamics in addition to the baseline model.

The Pearson correlation matrix is conducted for the interrelations of carotid energy PI, carotid flow PI, aortic energy PI, aortic pressure PI, and aortic flow PI. Correlations between carotid total, mean and pulsatile energy with aortic total, mean and pulsatile energy, aortic forward wave pulsatile energy transmitted into carotid artery, and $\Gamma_{Ao}$ are examined by using the Pearson correlation. The correlations between carotid mean and pulsatile energy and carotid energy PI are identified by general linear models. Causal mediation models to examine the relations between Zao and cognitive function are employed. Additionally, whether these associations are mediated by the carotid energy PI and carotid mean energy, or by the carotid flow PI and carotid mean flow is investigated. Furthermore, the associations between aortic pressure wave reflection coefficient $\Gamma_{Ao}$ and the cognitive function are explored. Also, whether these associations are mediated by the carotid energy PI and carotid mean energy, or by the carotid flow PI and carotid mean flow is examined. The statistic significant p value is dependent on the multiple comparison testing.

The Path analysis, involving causal mediation models, is conducted using the CALIS procedure in SAS 9.4. The performance of all models is assessed using the goodness of fit index (GFI). The significance level is established at a value of 0.05.

Results

Clinical characteristics and hemodynamic parameters of all 1858 participants are summarized in Table 1. Females have a higher average age, and HDL-cholesterol than males. Males have more hypertension and diabetes than females. Males have more university degrees than females. Men and women have a median Montreal cognitive score of 27.

TABLE 1

| Characteristics of the population | | | | | |
|---|---|---|---|---|---|
| Variables (mean ± std./%) | Females | | Males | | P value |
| N | 1183 | | 675 | | |
| Age, years | 61.2 | 9.9 | 59.4 | 11.4 | <0.0001 |
| Body mass index, kg/m2 | 23.5 | 3.4 | 24.8 | 3.1 | <0.0001 |
| Waist circumference, cm | 79.1 | 9.1 | 86.9 | 8.4 | <0.0001 |
| Triglycerides, mg/dl | 114.6 | 78.7 | 129.1 | 93.6 | 0.0007 |
| HDL-cholesterol, mg/dl | 63.5 | 16.1 | 51.1 | 12.3 | <0.0001 |
| LDL-cholesterol, mg/dl | 120.3 | 31.8 | 116.0 | 35.0 | 0.0089 |
| Total cholesterol, mg/dl | 208.2 | 35.6 | 193.1 | 38.2 | <0.0001 |
| Fasting glucose, mg/dl | 95.5 | 17.5 | 100.1 | 19.1 | <0.0001 |
| Medical history, n (%) | | | | | |
| hypertension, % | 26.54% | | 36.15% | | <0.0001 |
| Hypertensive medicine, % | 15.64% | | 15.85% | | 0.9031 |
| diabetes, % | 8.71% | | 13.78% | | 0.0006 |
| anti-diabetic medicine, % | 7.44% | | 11.56% | | 0.0028 |
| Education level, n (%) | | | | | <0.0001 |
| Elementary or below | 8.96% | | 2.22% | | |
| Junior school | 9.97% | | 7.70% | | |
| High school | 34.23% | | 25.48% | | |
| University or higher | 46.83% | | 64.59% | | |
| Brachial systolic blood pressure, mmHg | 123.1 | 17.7 | 128.8 | 16.7 | <0.0001 |
| Brachial diastolic blood pressure, mmHg | 72.5 | 9.3 | 78.9 | 9.8 | 0.0008 |

TABLE 1-continued

Characteristics of the population

| Variables (mean ± std./%) | Females | | Males | | P value |
|---|---|---|---|---|---|
| Carotid-femoral pulse wave velocity, m/sec | 12.0 | 3.3 | 12.6 | 4.0 | 0.2388 |
| $Z_{ao}$, dyne*s/cm$^5$ | 126.0 | 61.7 | 122.4 | 63.1 | <0.0001 |
| Aortic pressure wave reflection coefficient, $\Gamma_{Ao}$ | 0.11 | 0.06 | 0.10 | 0.06 | 0.0005 |
| Montreal cognitive assessment score, median (25%, 75%) | 27[26, 29] | | 27[26, 29] | | 0.9585 |

The carotid mean flow is found to be approximately 30.30% of the aortic mean flow. Additionally, the carotid pulsatile flow is observed to be around 10.200 of the aortic pulsatile flow. Consequently, the carotid flow PI is calculated to be approximately 34.500 of the aortic flow PI. The energy PI of the carotid artery is found to be 37.90 when compared to the aortic counterparts, as indicated in Table 2. A comparative analysis of flow and energy metrics between female and male at ascending aorta and CCA is summarized in Table 2. As expected, male exhibited higher mean and peak flow rate and total energy at both ascending aorta and carotid artery. Still, there are no significant differences between male and female in terms of energy pulsatility at both sites.

TABLE 2

Flow and energy related variables at ascending aorta and common carotid arteries

| Variables | Females | | Males | | P value |
|---|---|---|---|---|---|
| | Mean | SD | Mean | SD | |
| Ascending aorta | | | | | |
| mean pressure, mmHg | 90.9 | 12.0 | 96.9 | 11.8 | <0.0001 |
| pulse pressure, mmHg | 38.7 | 10.4 | 38.0 | 9.7 | 0.1070 |
| pressure pulsatility index | 0.42 | 0.09 | 0.39 | 0.09 | <0.0001 |
| Mean flow, mL/s | 79.4 | 20.7 | 87.7 | 24.6 | <0.0001 |
| Peak flow, mL/s | 300.8 | 70.6 | 345.4 | 84.7 | <0.0001 |
| Flow pulsatility index | 3.84 | 0.52 | 4.01 | 0.56 | <0.0001 |
| Total energy, mJ | 944.5 | 280.2 | 1088.7 | 323.0 | <0.0001 |
| Mean energy, mJ | 843.7 | 240.7 | 976.8 | 282.1 | <0.0001 |
| Pulsatile energy, mJ | 100.9 | 50.4 | 111.9 | 54.9 | <0.0001 |
| Energy pulsatility index | 0.12 | 0.04 | 0.11 | 0.04 | 0.0320 |
| Common carotid arteries | | | | | |
| Mean flow, mL/s | 22.6 | 5.0 | 25.2 | 5.8 | <0.0001 |
| Peak flow, mL/s | 28.2 | 7.8 | 36.8 | 11.7 | <0.0001 |
| Pulsatility index | 1.25 | 0.23 | 1.46 | 0.32 | <0.0001 |
| Total energy, mJ | 252.8 | 69.3 | 295.6 | 83.4 | <0.0001 |
| Mean energy, mJ | 241.9 | 65.5 | 283.3 | 79.1 | <0.0001 |

TABLE 2-continued

Flow and energy related variables at ascending aorta and common carotid arteries

| Variables | Females | | Males | | P value |
|---|---|---|---|---|---|
| | Mean | SD | Mean | SD | |
| Pulsatile energy, mJ | 10.9 | 6.0 | 12.3 | 7.1 | <0.0001 |
| Energy pulsatility index | 0.044 | 0.018 | 0.043 | 0.019 | 0.0933 |

Figure 4:
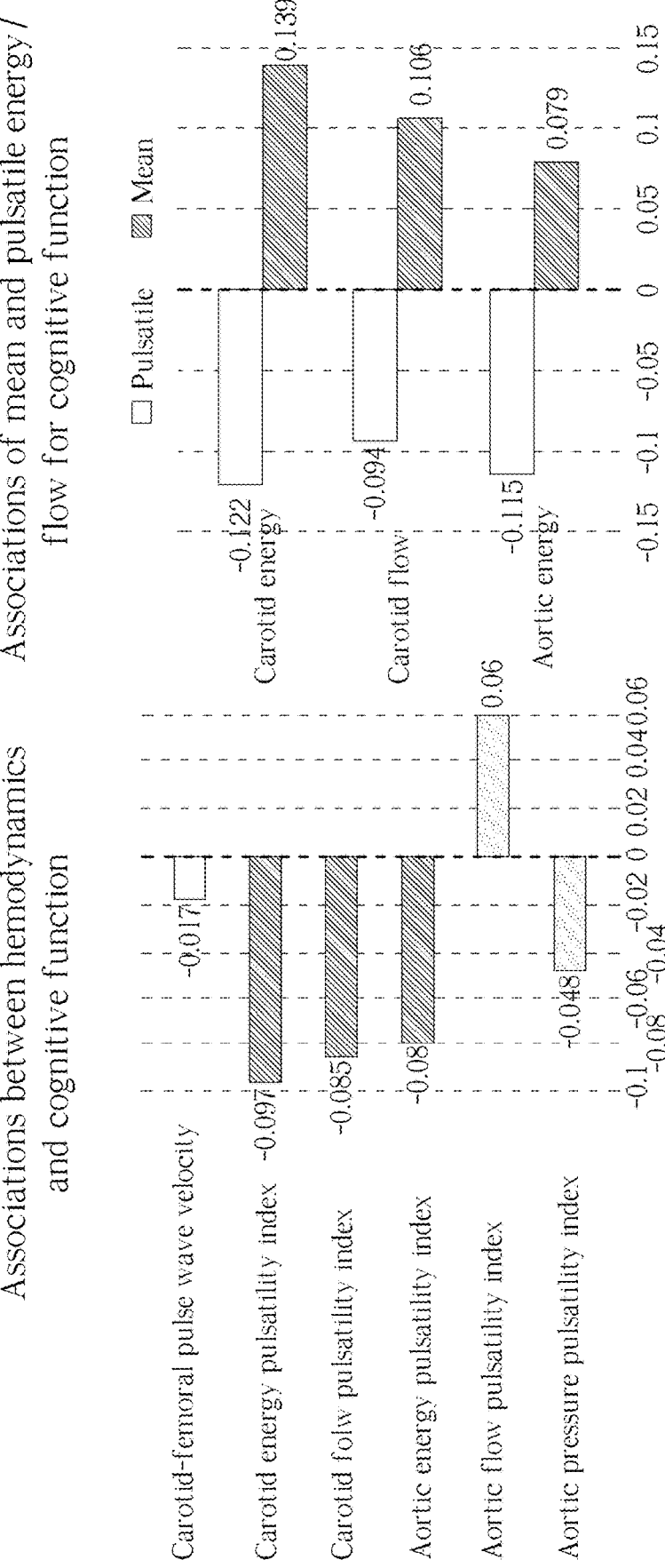
FIG. 4 is bar graphs illustrating differential aortic or carotid hemodynamics in relation to cognitive function in accordance with embodiments of the present disclosure. Left panel of FIG. 4 is a bar graph illustrating the correlation between hemodynamics and cognitive function in accordance with embodiments of the present disclosure. Right panel of FIG. 4 is a bar graph illustrating the correlation between cognitive function and mean energy and pulsatile energy in accordance with embodiments of the present disclosure. Coefficients of correlation are all adjusted for sex, age, and level of education. The histogram with slashes represents a p value less than 0.01, the dotted histogram represents a p value between 0.01 and 0.05, and the white histogram in the left panel of FIG. 4 represents a p value greater than 0.05.

The MoCA score is significant associated with variables, such as age, education level, blood pressure, fasting glucose levels, and lipid profiles. After adjusting for age, sex, educational attainment, and depression levels, only certain variables, namely peripheral mean pressure, waist circumference, body mass index, high density lipoprotein cholesterol, total cholesterol, and fasting blood sugar, continue to exhibit a significant association with MoCA. The associations between MoCA score and different hemodynamic parameters are displayed in Table 3. The MoCA scores demonstrate inverse relationships with the aortic mean, pulse and systolic pressure, and aortic energy PI, and carotid flow PI. Conversely, a positive correlation is observed with the carotid mean energy. As summarized in Table 3, the hemodynamic parameters of the carotid artery demonstrate a more robust correlation with the MoCA scores as compared to those of the aorta. Furthermore, the investigation reveals that parameters based on energy, specifically the mean and pulsatile energy in the carotid artery, along with the pulsatility index (PI) of energy, exhibit significantly stronger correlations with MoCA scores than any parameters based on pressure or flow, including mean, peak, and pulse pressure or flow in both the aorta and carotid arteries. Further analysis reveals that the carotid energy P emerged to have the most significant correlation with cognitive function (r=−0.097), after adjusting for various confounding factors, including age, gender, level of education, and various health indicators, as well as analyzing against conventional hemodynamic parameters, namely aortic or carotid systolic, mean and pulse pressure or flow. The second most significantly correlated parameter is the carotid flow PI (r=−0.085), followed by the aortic energy P (r=−0.080), as depicted in left panel of FIG. 4.

TABLE 3

Associations of flow and energy-related variables and carotid-femoral pulse wave velocity with MoCA score

| Variables | Crude | | Model A | | Model B | |
|---|---|---|---|---|---|---|
| | β | P value | β | P value | β | P value |
| Ascending aorta | | | | | | |
| mean pressure, mmHg | −0.069 | 0.0030 | 0.025 | 0.2588 | 0.044 | 0.0537 |
| pulse pressure, mmHg | −0.152 | <0.0001 | −0.038 | 0.0917 | −0.021 | 0.3676 |

TABLE 3-continued

| Associations of flow and energy-related variables and carotid-femoral pulse wave velocity with MoCA score | | | | | | |
|---|---|---|---|---|---|---|
| | Crude | | Model A | | Model B | |
| Variables | β | P value | β | P value | β | P value |
| pressure pulsatility index | −0.137 | <0.0001 | −0.064 | 0.0063 | −0.052 | 0.0262 |
| Mean flow, mL/s | −0.040 | 0.0833 | −0.030 | 0.1966 | −0.017 | 0.4788 |
| Peak flow, mL/s | −0.026 | 0.2540 | −0.012 | 0.5911 | −0.002 | 0.9364 |
| Flow pulsatility index | 0.013 | 0.5713 | 0.032 | 0.2353 | 0.0232 | 0.3916 |
| Total energy, mJ | −0.072 | 0.0020* | −0.021 | 0.3362 | −0.002 | 0.9367 |
| Mean energy, mJ | −0.056 | 0.0153 | −0.010 | 0.6366 | 0.009 | 0.7000 |
| Pulsatile energy, mJ | −0.132 | <0.0001* | −0.071 | 0.0014* | −0.054 | 0.0185 |
| Energy pulsatility index | −0.141 | <0.0001* | −0.088 | <0.0001* | −0.076 | 0.0006* |
| Common carotid arteries | | | | | | |
| Mean flow, mL/s | 0.083 | 0.0003* | 0.043 | 0.0529 | 0.038 | 0.0856 |
| Peak flow, mL/s | 0.039 | 0.0901 | −0.021 | 0.3677 | −0.013 | 0.5880 |
| Pulsatility index | −0.047 | 0.0435 | −0.084 | 0.0002* | −0.069 | 0.0022* |
| Total energy, mJ | 0.022 | 0.3412 | 0.047 | 0.0484 | 0.053 | 0.0253 |
| Mean energy, mJ | 0.0349 | 0.1323 | 0.0529 | 0.0248 | 0.058 | 0.0136 |
| Pulsatile energy, mJ | −0.133 | <0.0001* | −0.047 | 0.0524 | −0.033 | 0.1805 |
| Energy pulsatility index | −0.198 | <0.0001* | −0.1074 | <0.0001* | −0.093 | 0.0002* |
| Carotid-femoral pulse wave velocity, m/sec | −0.175 | <0.0001* | −0.0084 | 0.7545 | 0.00622 | 0.8182 |

β: standardized β regression coefficient
Model A: adjusted for age, sex, education, depression, and heart rate
Model B: adjusted for age, sex, education, depression, heart rate, body mass index, high density lipoprotein cholesterol, and glucose
*p value < 0.0033 (0.05/15) for multiple comparison In the comparative analysis presented in Table 4, it is found that, after adjusting for age, sex, and education, along with their respective pulsatility index (PI) indices, both the carotid flow P (as depicted in Model 1 of Table 4) and the aortic energy P (as depicted in Model 2 of Table 4) cease to be significantly associated with cognitive function. A stratified analysis by age is further performed. Due to the limited number of participants above the typical age threshold of 65 for older adults, the cutoff age to 60 years is adopted to classify the subjects into the older cohort and the younger cohort. The results reveal the relationship between hemodynamic parameters and MoCA varies between elderly and young populations. In at least one embodiment of the present disclosure, significant associations of hemodynamic parameters, particularly energetic hemodynamic parameters, are mainly seen in the older population.

TABLE 4

| The comparative associations of carotid energy pulsatility index, carotid flow pulsatility index, aortic energy pulsatility index with MoCA scores | | | |
|---|---|---|---|
| Multivariate model | Beta | (95% C.I.) | p value |
| Model 1 | | | |
| Age, years | −0.039 | (−0.052, −0.027) | <0.0001 |
| Sex, Male vs. Female | −0.428 | (−0.669, −0.188) | 0.0005 |
| Education, yrs | 0.306 | (−0.052, −0.027) | <0.0001 |
| Carotid energy pulsatility index | −10.249 | (−18.513, −1.984) | 0.0152 |
| Carotid flow pulsatility index | −0.3279 | (−0.822, 0.166) | 0.1934 |
| Model 2 | | | |
| Age, years | −0.036 | (−0.048, −0.024) | <0.0001 |
| Sex, Male vs. Female | −0.496 | (−0.714, −0.277) | <0.0001 |
| Education, yrs | 0.304 | (0.272, 0.336) | <0.0001 |
| Carotid energy pulsatility index | −12.865 | (−24.182, −1.549) | 0.0260 |
| Aortic energy pulsatility index | −0.405 | (−5.397, 4.587) | 0.8738 |
| Model 3 | | | |
| Age, years | −0.033 | (−0.045, −0.021) | <0.0001 |
| Sex, Male vs. Female | −0.403 | (−0.630, −0.176) | 0.0005 |

TABLE 4-continued

| The comparative associations of carotid energy pulsatility index, carotid flow pulsatility index, aortic energy pulsatility index with MoCA scores | | | |
|---|---|---|---|
| Multivariate model | Beta | (95% C.I.) | p value |
| Education, yrs | 0.306 | (0.274, 0.338) | <0.0001 |
| Carotid energy pulsatility index | −28.804 | (−41.206, −16.401) | <0.0001 |
| Aortic energy pulsatility index | 3.428 | (1.019, 5.836) | 0.0053 |
| Model 4 | | | |
| Age, years | −0.038 | (−0.050, −0.026) | <0.0001 |
| Sex, Male vs. Female | −0.543 | (−0.763, −0.323) | <0.0001 |
| Education, yrs | 0.304 | (0.272, 0.336) | <0.0001 |
| Carotid energy pulsatility index | −14.021 | (−20.443, −7.600) | <0.0001 |
| Aortic flow pulsatility index | 0.269 | (0.073, 0.464) | 0.0072 |

Table 5 summarizes the correlations of carotid mean energy, carotid energy PI, and carotid PI with aortic pressure, flow, energetic metrics and cf-PWV, $Z_{ao}$, and $\Gamma_{Ao}$. Notably, carotid mean energy correlates positively with both aortic mean (r=0.126) and peak flow (r=0.11), with all p<0.0001. The carotid energy PI also shows a positive correlation with aortic mean flow (r=0.104) and a weaker one with peak flow (r=0.082). Additionally, the carotid PI has robust positive associations, especially with aortic peak flow (r=0.186). Significant correlations are noted between $Z_{ao}$ and both carotid energy PI and carotid PI. Furthermore, there is an inverse relationship between the reflection coefficient at the aorto-carotid junction, $\Gamma_{Ao}$, and carotid energy PI and flow PI, whereas carotid mean energy positively correlates with $\Gamma_{Ao}$.

TABLE 5

| | Carotid mean energy | | Carotid energy pulsatility index | | Carotid pulsatility index | |
|---|---|---|---|---|---|---|
| Variables | Partial r | P value | Partial r | P value | Partial r | P value |
| Aortic mean pressure, mmHg | 0.499 | <0.0001 | 0.058 | 0.0137 | −0.065 | 0.0051 |
| Aortic pulse pressure, mmHg | 0.348 | <0.0001 | 0.736 | <0.0001 | 0.312 | <0.0001 |
| Aortic pressure pulsatility index | 0.097 | <0.0001 | 0.858 | <0.0001 | 0.418 | <0.0001 |
| Aortic mean flow, mL/s | 0.126 | <0.0001* | 0.104 | <0.0001* | 0.097 | <0.0001 |
| Aortic peak flow, mL/s | 0.110 | <0.0001* | 0.082 | 0.0004* | 0.108 | <0.0001 |
| Aortic flow pulsatility index | −0.018 | 0.452 | −0.033 | 0.1568 | 0.038 | 0.1047 |
| Aortic total energy, mJ | 0.330 | <0.0001* | 0.218 | <0.0001* | 0.113 | <0.0001 |
| Aortic mean energy, mJ | 0.333 | <0.0001* | 0.126 | <0.0001* | 0.064 | 0.0059 |
| Aortic pulsatile energy, mJ | 0.235 | <0.0001* | 0.639 | <0.0001* | 0.338 | <0.0001 |
| Aortic energy pulsatility index | 0.025 | 0.2921 | 0.822 | <0.0001* | 0.435 | <0.0001 |
| Carotid-femoral pulse wave velocity, m/sec | 0.205 | <0.0001* | 0.277 | <0.0001* | 0.130 | <0.0001 |
| $Z_{ao}$, dyne*s/cm$^5$ | 0.019 | 0.4116 | 0.350 | <0.0001* | 0.161 | <0.0001 |
| Aortic pressure wave reflection coefficient, $\Gamma_{Ao}$ | 0.364 | <0.0001* | −0.188 | <0.0001* | −0.360 | <0.0001 |

*p < 0.005 for multiple comparison

Figure 5:
FIG. 5 is a schematic diagram illustrating analysis of the causal mediation of the associations between aortic characteristic impedance ($Z_{ao}$) and Aortic pressure wave reflection coefficient and cognitive function in accordance with embodiments of the present disclosure. Upper left panel of FIG. 5 is a schematic diagram illustrating $Z_{ao}$ is indirectly associated with cognitive function through carotid energy pulsatility index, but not by carotid mean energy in accordance with embodiments of the present disclosure. $Z_{ao}$ does not have direct effect on cognitive function (beta=−0.0201, p=0.3591). Upper right panel of FIG. 5 is a schematic diagram illustrating $Z_{ao}$ is indirectly associated with cognitive function through carotid energy pulsatility index, but not by carotid mean energy in accordance with embodiments of the present disclosure. Carotid mean f low is not associated with cognitive function. Lower left panel of FIG. 5 is a schematic diagram illustrating aortic pressure wave reflection coefficient ($\Gamma_{Ao}$) is associated with cognitive function through carotid energy pulsatility index, and aortic pressure wave reflection coefficient ($\Gamma_{Ao}$) has not direct effect on cognitive function in accordance with embodiments of the present disclosure. Lower right panel of FIG. 5 is a schematic diagram illustrating aortic pressure wave reflection coefficient ($\Gamma_{Ao}$) is associated with cognitive function through carotid energy pulsatility index, and aortic pressure wave reflection coefficient ($\Gamma_{Ao}$) also has a direct effect on cognitive function (beta=0.0559, p=0.0166) in accordance with embodiments of the present disclosure.

The analysis presented in FIG. 5 clearly demonstrates the impact of carotid energy PI and carotid mean energy on MoCA scores. The impact of $Z_{ao}$ and $\Gamma_{Ao}$ on MoCA is solely mediated through energetic hemodynamic parameters, without any direct influence. On the other hand, the flow-based analysis places emphasis on the contribution of flow pulsatility to the MoCA, ascribing significant direct effects to both Zao (with borderline significance) and $\Gamma_{Ao}$.

In some embodiments, the present disclosure emphasizes the unique importance of energetic hemodynamic parameters in comprehending the connection between vascular health and cognitive function. The initial analysis reveals a clear beneficial relationship between carotid mean energy and cognitive function, while a negative relationship is observed with pulsatile energy. The present disclosure represents a painstaking effort to identify the carotid energy PI as a more effective hemodynamic indicator for cognitive function. Furthermore, after conducting a thorough evaluation of numerous energetic hemodynamic parameters related to the aorta and carotid artery, it has been established that the carotid energy PI emerges as the most prominent indicator for predicting the cognitive performance, surpassing all available conventional pressure- or flow-based parameters. Subsequently, an extensive investigation into the carotid energy PI and carotid mean energy, in relation to aortic flow and energy indices, aortic stiffness, aorto-carotid impedance mismatch, and organ perfusion is conducted.

In some embodiments, the aorto-carotid impedance mismatch has long been regarded playing a critical role in cognitive function. The present disclosure shows that an increase in proximal aortic stiffness is a contributing factor to the elevated pulsatile energy observed in the carotid arteries, whereas the influence of aortic stiffness, $Z_{ao}$, and the wave reflection coefficient, $\Gamma_{Ao}$, on MoCA predominantly manifests itself through energy metrics, rather than through direct effects. In contrast, a flow-based assessment underscores the fundamental importance of flow pulsatility in the MoCA. Significant direct effects are ascribed to both $Z_{ao}$ and $\Gamma_{Ao}$. However, it is conceivable that this assessment may have placed excessive emphasis on the importance of wave reflection in the pathophysiological connection between vascular health and cognitive impairment. Hence, the approach of the present disclosure, which is based on the concept of energy, focuses on the complex impact of energy pulsations on cognitive function. The approach of the present disclosure approach contributes to a comprehensive understanding of the interconnected relationship between vascular health and cognitive function.

The present disclosure comprehensively elucidates the fundamental mechanisms that govern the transfer of increased circulatory pulsatility from a stiffened aorta to cerebral circulation and demonstrated the connection and significant impact of the "impedance mismatch" phenomenon with cognitive function. The hemodynamic energy in carotid arteries is linked to aortic hemodynamic energy produced by the LV contraction and is inversely related to the reflection coefficient at the aorto-carotid junction, which is influenced by aortic and carotid admittance/compliance. During youth, aortic compliance exceeds carotid compliance, resulting in a high reflection coefficient known as "impedance mismatch". As individuals grow older, there is a noticeable increase in impedance "matching", which can be attributed to a greater increase in aortic impedance as compared to impedance of first-generation branch vessels. This impedance matching leads to heightened transmission of pressure and flow pulsatility into the cerebral circulation, ultimately strengthening the connection between the cardiac and cerebral structures and respective functions thereof. In at least one embodiment of the present disclosure, variations in connections may be attributed to the scarcity of individuals with cognitive decline in the younger population and the concept of impedance mismatch. Strong correlations between hemodynamic parameters, especially energetic ones, are predominantly observed in the elderly. These observations align with the gradual stiffening of the proximal aorta. Furthermore, analysis of the present disclosure comprehensively investigates the substantial impacts of the carotid energy PI and carotid mean energy on MoCA scores. This observation implies that the flow-based approach may potentially exaggerate the extent to which wave reflection contributes to the preservation of pulsatility, while simultaneously overlooking its influence in amplifying mean energy. By employing the energy-based methodology, it is possible to distinguish the heightened influence of energy pulsatility compared to mean energy on the MoCA, with $Z_{ao}$ playing a noteworthy role. Nevertheless, the contributions of protective effects resulting from reflections at the interface between the aorta and carotid artery are somewhat limited. The finding of the present disclosure is consistent with that of the AGES-Reykjavik Study, where the pulsatile power (pulsatile energy normalized by the period of a cardiac cycle) is negatively associated with cognitive function. It is further demonstrated that the counteractive effect of the positive association between carotid mean energy and cognitive function is comparable to the negative association between carotid pulsatile energy and MOCA score (standardized Beta: 0.117 vs. −0.109).

Strengths of the Present Disclosure

There are several strengths in the present disclosure. First, the present disclosure shows that the carotid mean energy and the pulsatile energy are positively and negatively associated with cognitive function, respectively. Second, through extensive evaluation of exhaustive aorto-carotid hemodynamic parameters, it is concluded that the carotid energy PI is the single most effective hemodynamic parameter for predicting cognitive function, much more effective than any other available energetic hemodynamic parameters proposed previously. Third, the study populations of the present disclosure have a broad age-range between 31 and 96 years old, not limited to aging population.

Conclusion

In at least one embodiment of the present disclosure, energetic hemodynamic parameters, especially carotid mean energy, and carotid energy PI, provide a more robust framework for understanding the vascular-cognitive *nexus* compared to conventional measures.

Perspectives

In summary, the present disclosure demonstrates a robust association between energetic hemodynamic parameters and cognitive function. A strong association between the presence of an increased carotid energy PI, which is characterized by heightened carotid pulsatile energy and decreased carotid mean energy, and impaired cognitive performance, as assessed by the MoCA is demonstrated. The present disclosure provides substantial evidence to support the notion that carotid energy PI and carotid mean energy are more dependable indicators of cognitive decline compared to conventional hemodynamic parameters that rely on flow or pressure measurements. This discovery affirms the enhanced explanatory potential of energetic hemodynamic parameters in the association between vascular health and cognitive function. Future emphasis may not be on arterial pressure or blood flow, but rather on energy, which may become the standard unit of measurement.

In at least one embodiment of the present disclosure, the carotid energy PI may be a promising therapeutic target because of significant correlation with cognitive function thereof. To potentially slow down the progression of vascular dementia, it is recommended to lower carotid energy PI by reducing carotid pulsatile energy, increasing aortic compliance, and decreasing carotid/cerebral resistance.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for estimating energetic hemodynamic parameters, comprising:

an ultrasound device obtaining a vascular diameter and a blood flow waveform from a subject, wherein the ultrasound device has an ultrasound probe;

obtaining a blood flow velocity of the subject according to the blood flow waveform;

a processor providing a volumetric flow rate, a pulse wave velocity (PWV), and a blood pressure waveform of the subject; and the processor obtaining the energetic hemodynamic parameters according to the vascular diameter, the blood flow waveform, the blood flow velocity, the volumetric flow rate, the pulse wave velocity (PWV), and the blood pressure waveform, wherein:

the processor obtaining the volumetric flow rate according to formula I $$\pi \int_{-r_0}^{r_0} v(r) r \, dr, \tag{I}$$

wherein:

$r_0$ is an initial vascular radius calculated from the vascular diameter;

$v(r)$ is a blood flow velocity polynomial;

$v$ is the blood flow velocity;

$r$ is a vascular radius; and $dr$ is an infinitesimal change or an increment in the vascular radius: or the processor obtaining the pulse wave velocity (PWV) according to formula II:

$$y = ax + b \tag{II},$$

wherein:

$y$ is the volumetric flow rate (Q);

$x$ is a vascular cross-sectional area (A);

$a$ is the pulse wave velocity (PWV); and $b$ is a constant: or the processor obtaining the blood pressure waveform according to formula III:

$$P_n = P_0 + \frac{\rho c^2}{A_0} \sum_{i=1}^{n} \Delta A_i, \tag{III}$$

wherein:

$n$ is a n-th sampled point;

$P_n$ is a blood pressure at the n-th sampled point;

$P_0$ is an end diastolic pressure;

$\rho$ is a blood density;

23 c is the pulse wave velocity (PWV);

A is a vascular cross-sectional area (A);

$A_0$ is an initial vascular cross-sectional area; and $\Delta A_i = A_i - A_{i-1}$.

2. The method of claim 1, wherein the ultrasound device obtaining the vascular diameter and the blood flow waveform by the ultrasound probe solely.

3. The method of claim 1, further comprising the ultrasound probe placing at an artery of the subject.

4. The method of claim 3, wherein the artery is an elastic artery or a muscular artery.

5. The method of claim 1, wherein the ultrasound device implements ultrasound brightness mode (B-mode) imaging and/or ultrasound color Doppler mode imaging.

6. The method of claim 5, wherein the ultrasound device obtains the vascular diameter by the ultrasound brightness mode (B-mode) imaging.

7. The method of claim 5, wherein the ultrasound device obtains the blood flow waveform by the ultrasound color Doppler mode imaging.

8. A system for estimating energetic hemodynamic parameters, comprising:

an ultrasound device having an ultrasound probe and configured to obtain a vascular diameter and a blood flow waveform from a subject; and a processor coupled to the ultrasound device and configured to:

obtain a blood flow velocity of the subject according to the blood flow waveform;

provide a volumetric flow rate, a pulse wave velocity (PWV), and a blood pressure waveform of the subject; and obtain the energetic hemodynamic parameters according to the vascular diameter, the blood flow waveform, the blood flow velocity, the volumetric flow rate, the pulse wave velocity (PWV), and the blood pressure waveform;

wherein the processor is configured to:

obtain the volumetric flow rate according to formula I $$\pi \int_{-r_0}^{r_0} v(r) r \, dr, \tag{I}$$

wherein:

$r_0$ is an initial vascular radius calculated from the vascular diameter;

24 v(r) is a blood flow velocity polynomial:

v is the blood flow velocity;

r is a vascular radius; and dr is an infinitesimal change or an increment in the vascular radius: or obtain the pulse wave velocity (PWV) according to formula II:

$$y = ax + b \tag{II},$$

wherein:

y is a volumetric flow rate (Q);

x is a vascular cross-sectional area (A);

a is the pulse wave velocity (PWV); and b is a constant; or obtain the blood pressure waveform according to formula III:

$$P_n = P_0 + \frac{\rho c^2}{A_0} \sum_{i=1}^{n} \Delta A_i, \tag{III}$$

wherein:

n is a n-th sampled point;

$P_n$ is a blood pressure at the n-th sampled point;

$P_0$ is an end diastolic pressure;

$\rho$ is a blood density;

c is the pulse wave velocity (PWV);

A is a vascular cross-sectional area (A);

$A_0$ is an initial vascular cross-sectional area; and $\Delta A_i = A_i - A_{i-1}$.

9. The system of claim 8, wherein the ultrasound device is configured to obtain the vascular diameter and the blood flow waveform by the ultrasound probe solely.

10. The system of claim 8, wherein the vascular diameter and the blood flow waveform are obtained from an artery of the subject.

11. The system of claim 9, wherein the artery is an elastic artery or a muscular artery.

12. The system of claim 8, wherein the ultrasound device is configured to implement ultrasound brightness mode (B-mode) imaging and/or ultrasound color Doppler mode imaging.

13. The system of claim 12, wherein the ultrasound device is configured to obtain the vascular diameter by the ultrasound brightness mode (B-mode) imaging.

14. The system of claim 12, wherein the ultrasound device is configured to obtain the blood flow waveform by the ultrasound color Doppler mode imaging.

* * * * *